United States Patent [19]
Thomson

[11] Patent Number: 5,377,865
[45] Date of Patent: Jan. 3, 1995

[54] DISPENSER FOR FLAT OBJECTS
[75] Inventor: Graham A. Thomson, London, England
[73] Assignee: Unilever Patent Holdings B.V., AT Vlaardingen, Netherlands
[21] Appl. No.: 50,406
[22] PCT Filed: Sep. 24, 1992
[86] PCT. No.: PCT/OB92/01756
  § 371 Date: May 11, 1993
  § 102(e) Date: May 11, 1993
[87] PCT Pub. No.: WO93/06207
  PCT Pub. Date: Apr. 1, 1993
[30] Foreign Application Priority Data
  Sep. 25, 1991 [EP] European Pat. Off. ............ 91308723
[51] Int. Cl.6 .............................................. B65H 3/44
[52] U.S. Cl. ......................................... 221/93; 53/258
[58] Field of Search ............... 221/93, 94, 265, 206; 53/254, 258

[56] References Cited
U.S. PATENT DOCUMENTS 2,947,444  8/1960  Taylor et al. ........................ 221/93
3,260,337  7/1966  Greenwald et al. ................. 221/93
3,836,047  9/1974  Darpentigny et al. ............... 221/93
3,863,426  2/1975  Courvalin ............................. 53/237
4,042,145  8/1977  Ehrlich ................................ 221/94

Primary Examiner—Kenneth W. Noland
Attorney, Agent, or Firm—Cushman Darby & Cushman

[57] ABSTRACT

A dispenser for dispensing flat objects, particularly susceptibility or sensitivity test discs (38), from a stack of similar objects housed in a cartridge (22) comprises a body portion (10); a plurality of receptacles (20) within the body portion, each receptacle being adapted to receive a respective object-containing cartridge; a plurality of dispensing ports (32), one associated with each receptacle; a plurality of tamping pins (50), one associated with each dispensing port, for tamping an object through the associated dispensing port; a transport plate arranged for rotary motion to transport an object from each cartridge in a receptacle to a dispensing position in alignment with the associated tamping pin and dispensing port; and a retaining plate (44) fixed with respect to the receptacles, for retaining the objects in position during transport from a cartridge to the associated dispensing position.

11 Claims, 7 Drawing Sheets

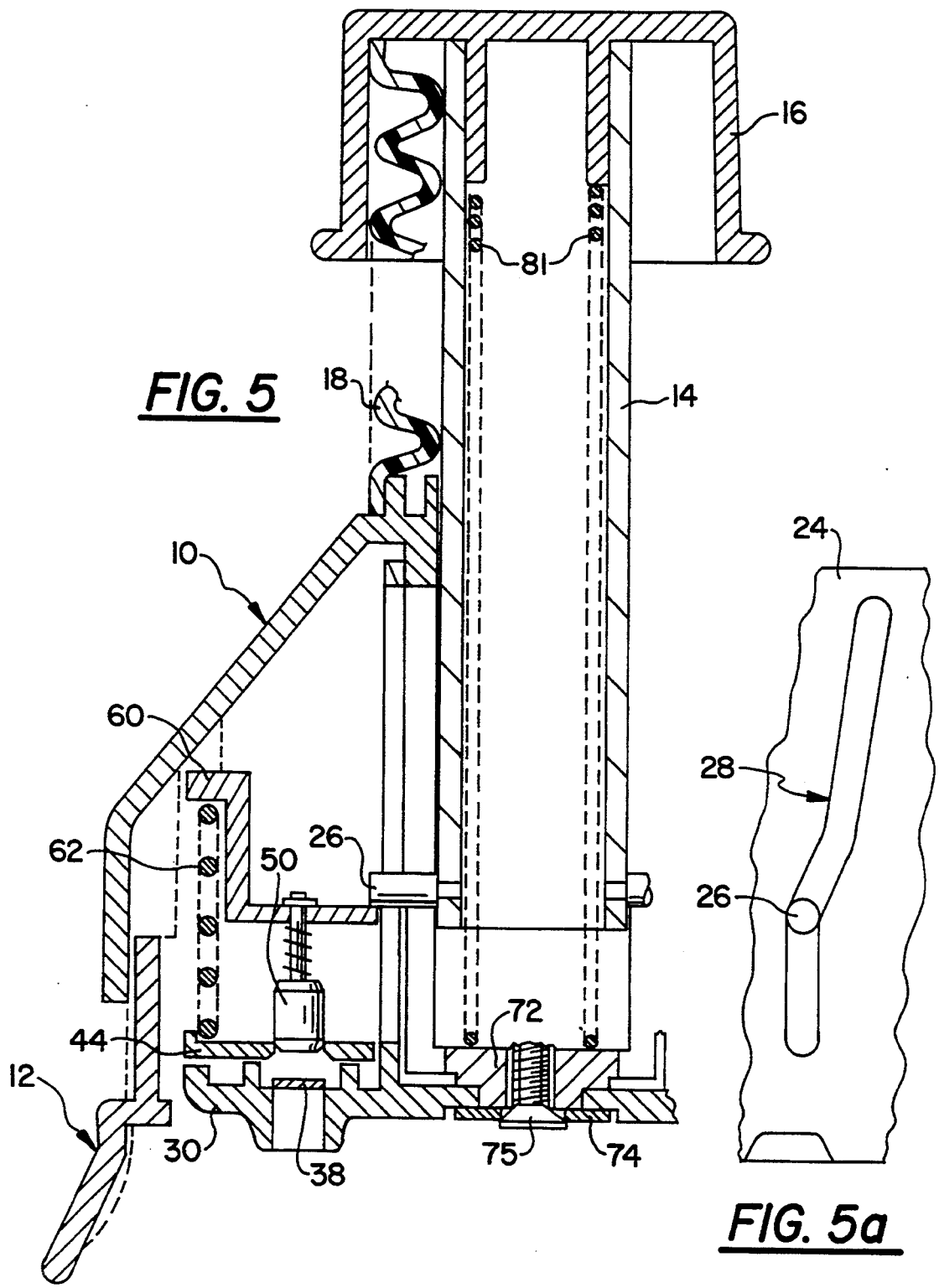

DISPENSER FOR FLAT OBJECTS

FIELD OF INVENTION

This invention concerns a dispenser for flat objects, and relates to a dispenser for dispensing flat objects from a stack of similar objects housed in a cartridge, and has particular application in dispensing susceptibility or sensitivity test discs impregnated with a substance such as an antibiotic.

BACKGROUND TO THE INVENTION

In sensitivity testing of samples of organisms, sensitivity discs impregnated with different substances, such as various antibiotics, are dispensed onto the surface of a culture medium, e.g. a thin layer of agar gel, in a receiving container such as petri dish. Such discs typically comprise a circular piece of absorbent material such as blotting paper, about 0.5 mm thick, and are conventionally supplied in a stack, e.g. of 50 discs, in an elongate cylindrical cartridge, with the discs biased to an exit end of the cartridge by means of an internal coil spring.

A variety of dispensers are known and commercially available for dispensing discs from such cartridges, including a variety of different designs of dispensers for simultaneously dispensing a plurality of discs in a predetermined pattern from respective cartridges. See, for example, U.S. Pat. No. 4,042,145 and U.S. Pat. No. 3,836,047.

The invention aims to provide a novel construction of dispenser for flat objects that is robust and reliable in operation.

SUMMARY OF THE INVENTION

In accordance with the present invention, there is provided a dispenser for dispensing flat objects from a stack of similar objects housed in a cartridge, comprising: a body portion; a plurality of receptacles within the body portion, each receptacle being adapted to receive a respective, object-containing cartridge; a plurality of dispensing ports, one associated with each receptacle; a plurality of tamping pins, one associated with each dispensing port, for tamping an object through the associated dispensing port; transport means arranged for rotary motion to transport an object from each cartridge in a receptacle to a dispensing position in alignment with the associated tamping pin and dispensing port; and retaining means fixed with respect to the receptacles, for retaining the objects in position during transport from a cartridge to the associated dispensing position.

For convenience, the explanation which follows assumes that objects are to be dispensed in a downwards direction, as will generally be the case in practice, but it is to be understood that the dispenser could also be used to dispense articles upwardly. Reference to orientation in the following explanation should thus be construed accordingly.

The dispensing ports are preferably initially rotationally offset with respect to the associated tamping pins, and in this case the transport means conveniently comprises a transport plate arranged for rotary motion.

The dispensing ports are preferably carried by the transport plate, e.g. by being integrally formed therewith, extending downwardly from the lower face of the plate. In this case, the lowermost object in a cartridge is initially located in position in an associated dispensing port, and on movement of the transport plate the dispensing port and associated object are moved into alignment with the associated tamping pin, ready for tamping. The dispensing ports are preferably dimensioned to have a diameter slightly less than the diameter of the discs to be dispensed so that the disc will sit on the top of the ports.

The transport plate preferably includes means for retaining and guiding the object in position during transport; conveniently the upper face of the transport plate is formed with an upwardly extending rim to engage the base of the associated cartridge and to receive the lowermost object in the cartridge, and includes an adjacent pushing face the engage an edge of the object and push the object with the transport plate on transport movement.

The retaining means conveniently comprise a retaining plate, located above the transport means, to contact the upper faces of the objects during transport. The retaining plate is preferably in the form of a disc with a first series of apertures through which ends of the cartridges pass and a second series of apertures, interposed between the first series, through which the tamping pins pass.

The tamping pins are conveniently actuated by a tamping plate arranged for downward movement in the body portion when the objects are in appropriate dispensing positions.

The dispenser conveniently includes a plunger actuator mechanism for causing appropriate movement of the components. The mechanism desirably includes a rotary actuating tube, fixed with respect to the transport means and including one or more cam slots each for receiving an actuating pin fixed with respect to a plunger. The or each slot is shaped such that downward movement of the plunger relative to the actuating tube causes initial rotary motion of the actuating tube and hence of the attached transport means, moving objects to the dispensing position. Subsequent downwards movement of the plunger causes vertical movement of the or each pin, in a vertical portion of the associated slot, with the pins engaging the dispensing plate and causing downwards dispensing movement of the tamping pins, resulting in dispensing of the objects, generally onto a receiving surface therebelow.

Such cam slots preferably include three sections: a first slightly inclined portion designed to give a good mechanical advantage on initial movement where the highest load is required; a second more inclined portion for causing rotation under conditions in which load is less; and a third vertical portion for downwards dispensing actuation of the tamping pins.

The plunger is conveniently biased to return to its initial, start position, e.g. by means of a suitable compression spring.

A separate return spring is preferably associated with the tamping plate, desirably located between the tamping plate and retaining plate. Both of these plates are fixed in rotation so that no twisting of the spring occurs during use.

The plunger is desirably fitted with a large end cap to facilitate ease of operation.

The tamping pins are preferably spring mounted so as to have a degree of vertical resilience, to accommodate irregularities in a receiving surface.

The dispenser enables simultaneous dispensing of an object from each dispensing port in a predetermined pattern. Typically six or eight dispensing ports are provided in a circular arrangement, but other arrangements e.g. twelve dispensing ports are also possible.

A gaiter, conveniently of resilient corrugated material, is desirably located around the upper portion of the plunger, between the body portion and end cap, to prevent ingress of dirt to the dispensing mechanism and possibly also for aesthetic reasons.

The dispenser finds particular application in the dispensing of sensivity or susceptibility test discs impregnated with substances such as antibiotics. As noted above, such discs are commonly supplied in a cylindrical cartridge in which a stack of circular discs of blotting paper, each about 0.5 mm thick, is spring biased to a dispensing aperture at one end of the cartridge. Such cartridges are of standard configuration and are widely available commercially.

Reliability of a dispensing device is important in such applications: on each dispensing action it is essential that a disc is dispensed from each cartridge, otherwise the test will be ineffective and the sample is thus wasted.

Antibiotic disc dispensers in accordance with the present invention have been found to function very well in practice. They are easy and reliable to use and there was found to be little or no tendency of the mechanism to stick in use, unlike certain prior art designs.

The dispenser may include a removable base for height adjustment purposes. The base preferably has a stepped upper face adapted to be engaged by inwardly extending longitudial ribs in the body portion such that relative rotation of the body and base results in adjustment in the height of the base above a surface. The outer face of the base preferably includes a plurality, e.g. 4, of series of vertical grooves or slots, so that the body can be positively located and retained on the base in any desired position of height adjustment by sliding the body downwardly on to the base with each rib engaging a selected groove of the associated series. The arrangement enables height adjustment to be effected without the need for tools. Such a height adjustment arrangement enables the dispenser to be adjusted to accommodate, for example, different gel thicknesses in petri dishes.

More than one base may be provided for a particular dispenser, intended for different end uses, for example with petri dishes of different diameters.

The dispenser may be provided with a casing, which is preferably of two-part form comprising a base and a top interconnected, e.g., by a bayonet fit. The casing base may include internal formations such that the casing can accommodate dispensers when fitted with height adjustment bases of different sizes. The casing cover preferably includes a large flat top area for labelling purposes. A dessicant material may be located in the casing, e.g. in a cavity in the base, in appropriate conditions, for example for use with dispensers containing cartridges of susceptibility discs.

A preferred embodiment of the invention in the form of a dispenser for use with cartridges of susceptibility test discs bearing antibiotics will now be described, by way of illustration, and with reference to the accompanying drawings in which:

FIGS. 5 and 5a are views similar to FIGS. 4 and 4a, with a mechanism in an intermediate position;

DETAILED DESCRIPTION OF THE DRAWINGS

The drawings illustrate a dispenser for dispensing susceptibility test discs bearing reagents such as antibiotics from cartridges of a form that is widely available commercially.

Figure 1:
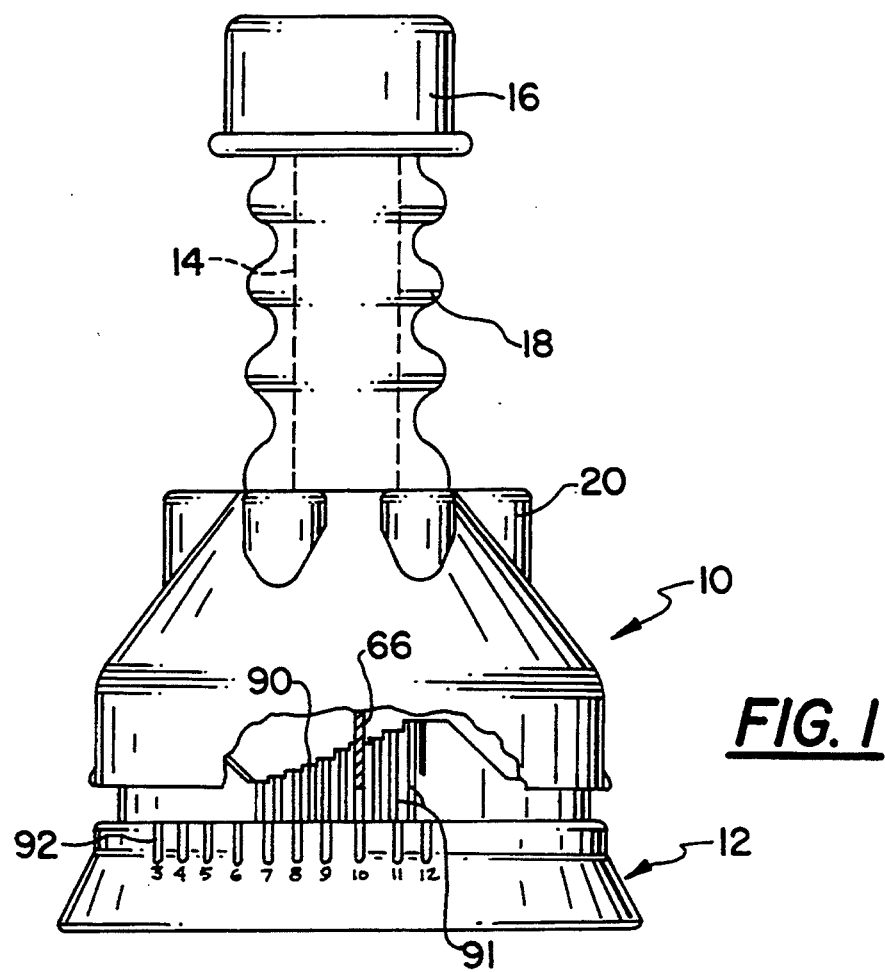
FIG. 1 is a side view of the dispenser, shown partly cut away.
Figure 2:
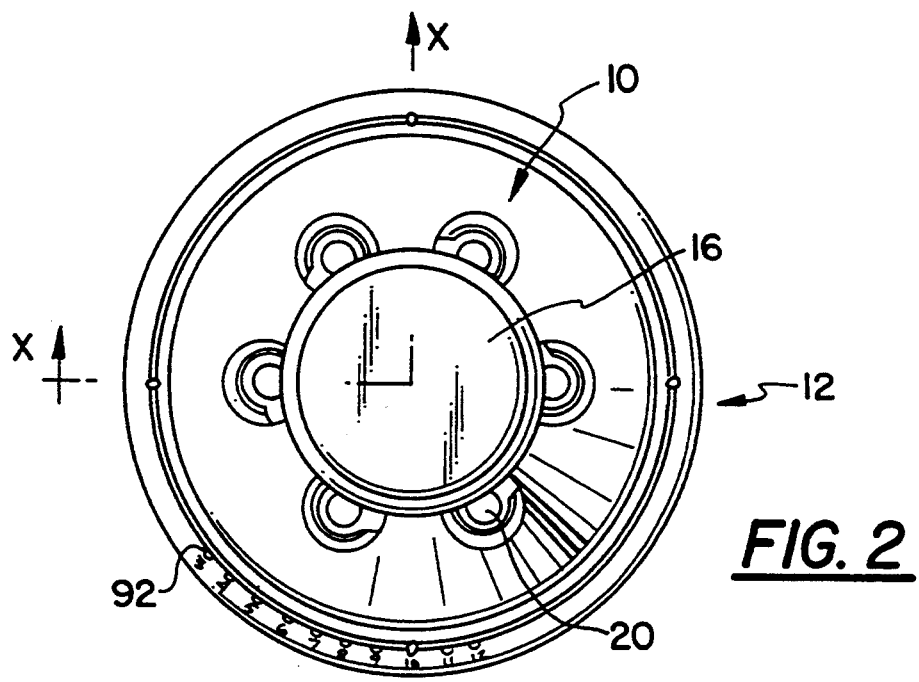
FIG. 2 is a top plan view of the dispenser.

With reference to FIGS. 1 and 2, the illustrated dispenser comprises a body portion 10 in which the dispensing mechanism is mainly housed; a removable base 12 for height adjustment purposes as will be described below; and an actuating plunger 14 fitted with an end cap 16 and surrounded by a resilient corrugated gaiter 18. Body portion 10 includes six similar tubular receptacles 20 each for receiving a cartridge 22 (FIG. 4) containing a stack of sensitivity discs engaged by a spring biased plunderer and urged towards a dispensing aperture. The disc-containing cartridges are of conventional construction, e.g. as supplied by Oxoid Limited, Basingstoke, Hampshire, England.

Figure 3:
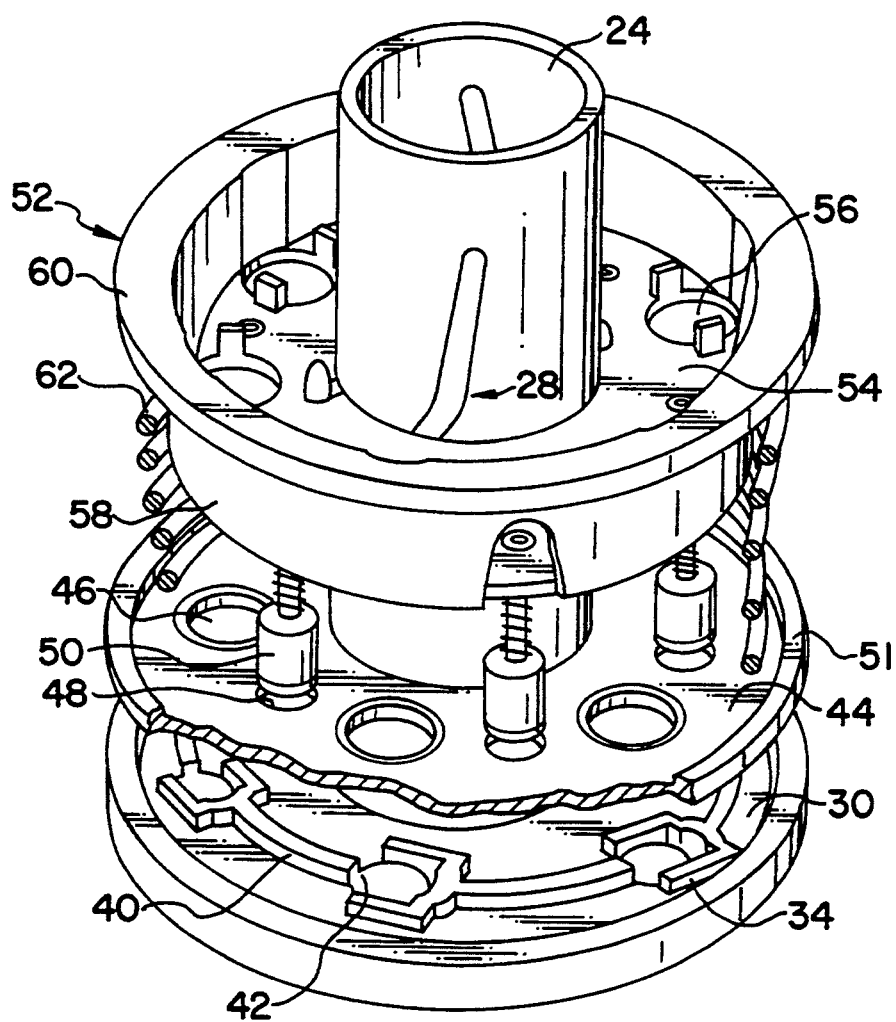
FIG. 3 is a diagrammatic exploded view, to an enlarged scale, of certain components of the dispenser.
Figure 4:
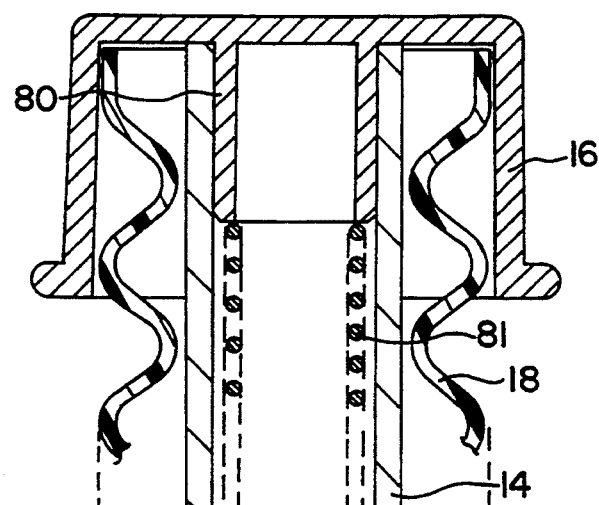
FIG. 4 is a partial sectional view along line X—X in FIG. 2, with the mechanism in a start or rest position.
Figure 4A:
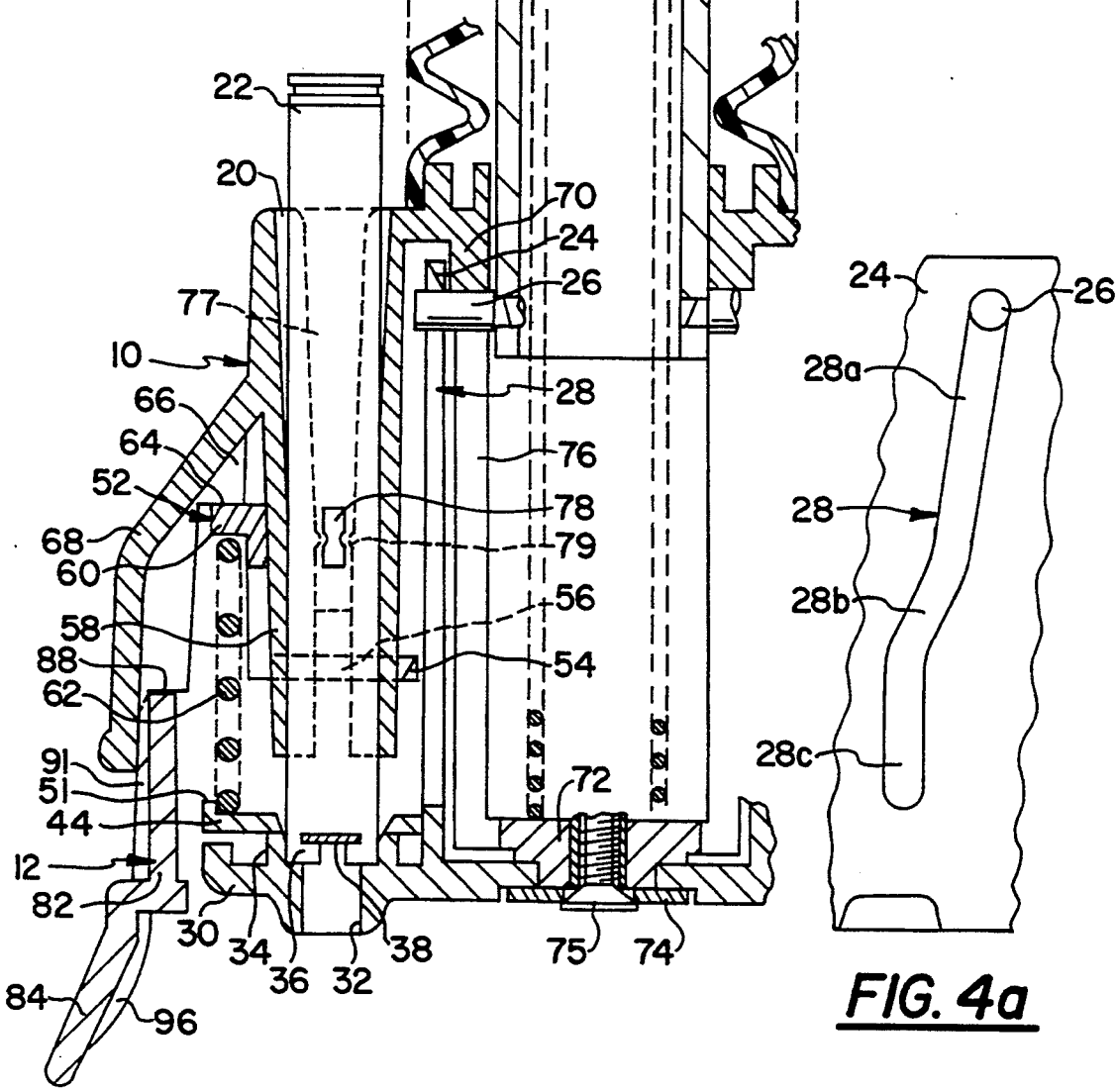
FIG. 4a is a fragmentary view illustrating the position of an actuating pin and cam slot in the condition of FIG. 4.

Referring to FIGS. 3 and 4, the dispensing mechanism comprises a rotatable actuating tube or sleeve 24 of larger diameter than plunger 14. Sleeve 24 is connected to the lower end of the plunger 14 by means of four actuating pins 26 extending radially outwardly from the plunger 14 and engaging in respective cam slots 28 machined in the sleeve 24. Each slot 28 includes an upper portion 28a of shallow slope, and intermediate portion 28b of steeper slope and a lower vertical portion 28c.

The lower end of sleeve 24 is formed integrally with a revolving transport plate 30. The transport plate is of generally annular configuration and includes 6 downwardly extending dispensing ports 32 the upper end of each of which is partially surrounded by a part circular upstanding rim 34. The dispensing ports are dimensioned to have a diameter slightly less than the diameter discs 38 to be dispersed so that the discs sit in the top of the port. Rim 34 engages the base of an associated cartridge 22 and receives retaining lugs 36 of the cartridge and also the lower most disc 38 retained thereby in the cartridge (FIG. 4). A respective upstanding rib 40 extends from each rim 34 and terminates in a front face 42 for engaging the edge of an adjacent disc 38 and pushing the disc to move with plate 30 on rotation, as will be described below.

A retaining plate 44 is located above the transport plate 30. Plate 44 is of generally annular configuration and includes six larger circular apertures 46 through which cartridges 22 extend, interspersed with six smaller circular apertures 48 each for receiving a respective tamping pin 50. Plate 44 includes an upstanding peripheral rim 51.

The tamping pins 50 extend downwardly from a dispensing plate or plunger bearing plate 52. Plate 52 includes an inner lower annular portion 54, with six circular apertures 56 through which lower portions of the cartridge-receiving receptacles 20 pass; an upstanding cylindrical side wall portion 58; and an outwardly extending flange portion 60. The tamping pins 50 are secured to the underside of portion 54, spaced midway between adjacent apertures 56, and are spring mounted to be resiliently displaceable to a limited degree with respect to the plate 52, for reasons to be described below.

A compression spring 62 is located between retaining plate 44 and flange portion 60 of dispensing plate 52 and acts to bias dispensing plate 52 upwardly to the position shown in FIG. 4, in which flange portion 60 engages a shoulder portion 64 on each of four stepped ribs 66 extending inwardly from a lower, outer skirt portion 68 of body portion 10. Plate 44 and plate 52 are both rotationally stationary during dispensing action, as will be discussed below, so that no twisting action is applied to the spring 62.

Body portion 10 also includes an inner tubular portion 70, the upper end of which surrounds plunger 14 with a sliding fit, and the lower end of which carries a bearing member 72. Bearing member 72 fits into a circular opening in the centre of transport plate 30, being secured in place by means of washer 74 and screw 75, so as to permit relative rotation between member 72 (which remains stationary during operation of the dispenser) and transport plate 30. Tubular portion 70 includes four elongate vertical slots 76 through which the actuating pins 26 pass for vertical sliding movement.

The cartridge receptacles 20 are formed in the body portion 10, and each comprises a slightly tapering cylindrical aperture including a tapering slot 77 down which is slid a protruding locking peg 78 on a cartridge 22. The slot includes protruding teeth 79 for engaging in mating recesses in the locking peg, for locating and locking the cartridge in position in the receptacle.

End cap 16 is a push fit in the upper end of plunger 14, with an insert 80 in the cap forming a tight friction fit within the plunger.

A compression spring 81 is located within the plunger 14 and body portion 10, extending between cap insert 80 and end cap 72, and acts to bias the plunger upwardly to the start or rest position shown in FIG. 4.

Base 12 includes a cylindrical upper portion 82 and a flared lower skirt portion 84. Upper portion 82 of base 12 is dimensioned to fit within the lower portion 68 of body portion 10.

The upper face of portion 82 engages a lower shoulder 88 on each rib 66. For height adjustment purposes, this face includes four similarly stepped regions 90 as shown in FIG. 1. A respective vertical groove or slot 91 in the outer face of portion 82 is associated with each step of region 90, so there are four series of varying length grooves 91. Each rib 66 can engage in a selected groove each series of grooves, so that the body portion can be positively located and retained in any desired position of height adjustment by rotating base 12 relative to body portion 10 and sliding the body portion downwardly onto the base with each rib engaging a selected groove of the associated series of grooves. The arrangement enables easy adjustment of the height of body portion 10 and hence the dispensing mechanism, enabling adjustment of the dispenser to accommodate use with gels of different thicknesses. No tools are required for this adjustment. Markings 92 (FIG. 1) are provided on the base to indicate different height positions.

Figures 6, 6A:
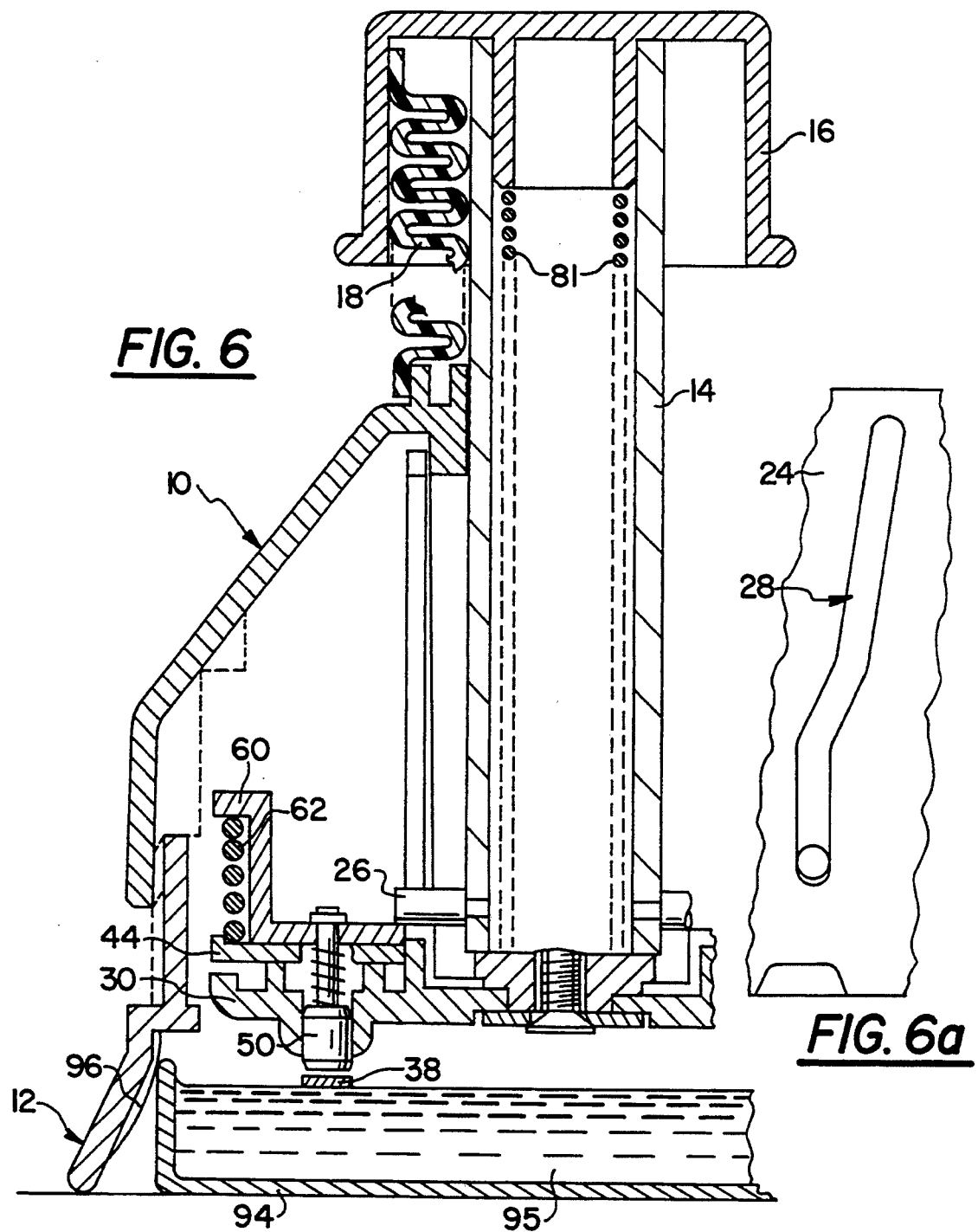
FIGS. 6 and 6a are views similar to FIGS. 4 and 4a, with the mechanism in an end or dispensed position, additionally illustrating a petri dish.

Skirt portion 82 is dimensioned to fit around a petri dish 94, as shown in FIG. 6, with the side wall of the dish engaging inwardly extending ribs 96 on the base skirt portion. The dispenser may be provided with two alternative bases, of different lower diameter, for use with petri dishes of different standard sizes, for example 90 mm and 100 mm. Petri dish 94 is shown containing a layer of agar gel 95.

Figure 11:
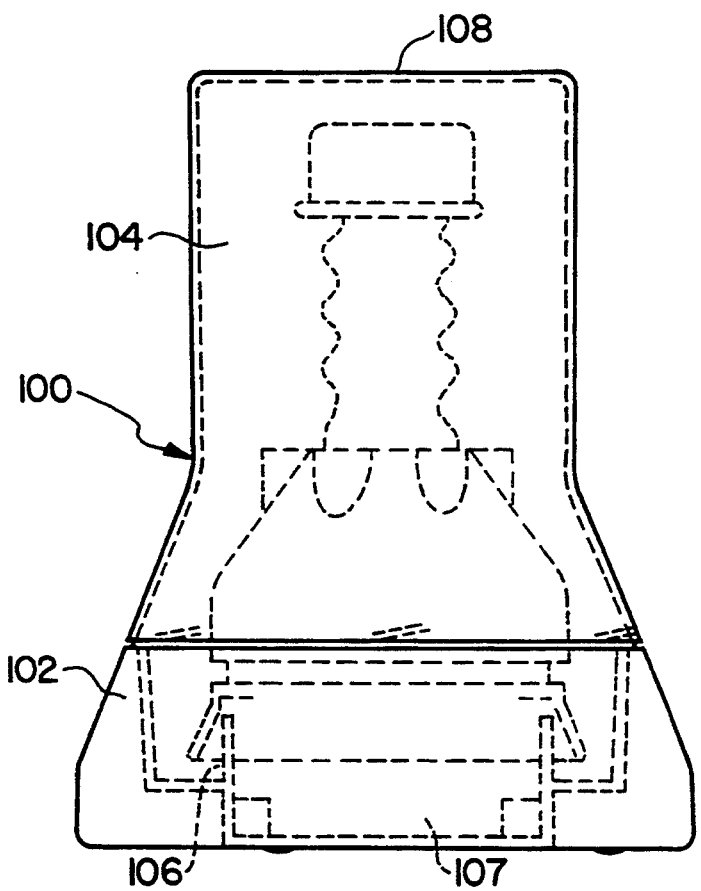
FIG. 11 illustrates a casing with the dispenser located therein

The dispenser is provided with a storage case 100, as shown in FIG. 11, comprising a base 102 and a cap 104 which are releasably secured together by a bayonet fitting. The base 102 includes an upstanding internal circular collar 106 so that it can accommodate dispensers fitted with both sizes of base. The smaller base engages the collar 106 as shown, and the larger size base engages the case base side wall. A sachet (not shown) containing a dessicant material may be located in recess 107 in base 102. The cap 104 includes a large, flat top 108 on which information can be readily marked, e.g. on a removable lable.

The dispenser components are all made of opaque acetal, with the exception of the plunger which is of steel, but may be of other metals. The base of the case is of opaque ABS and the top of the case is of polycarbonate. The angled slots 28 are machined, but the components are otherwised formed by moulding.

The dispenser, without base, has an overall height in the rest position of about 130 mm and an overall diameter of about 100 mm.

In use, six disc-containing cartridges 22 are located in the six receptacles 20 and locked in position by use of locking pegs 78.

Figure 7:
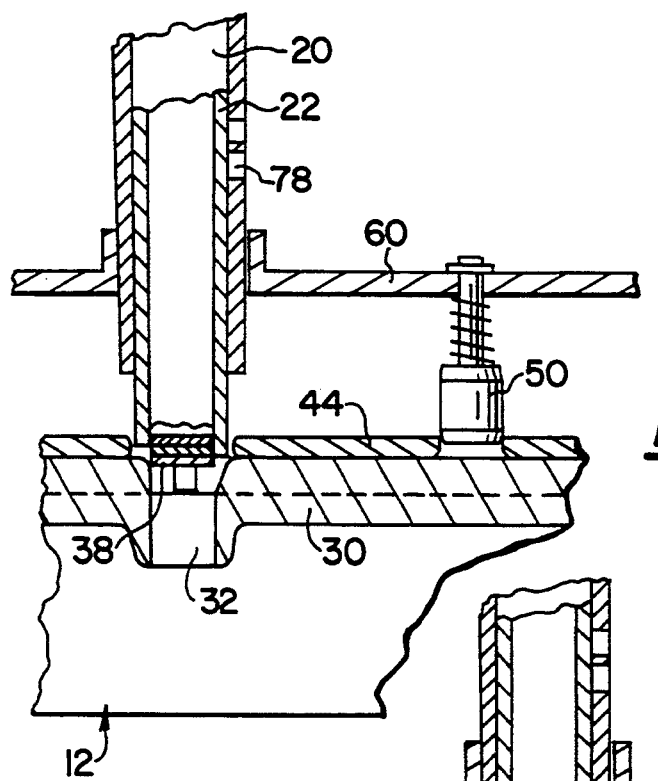
FIG. 7 is a diagrammatic view illustrating the position of various components, with the mechanism in the start or rest position.
Figure 8:
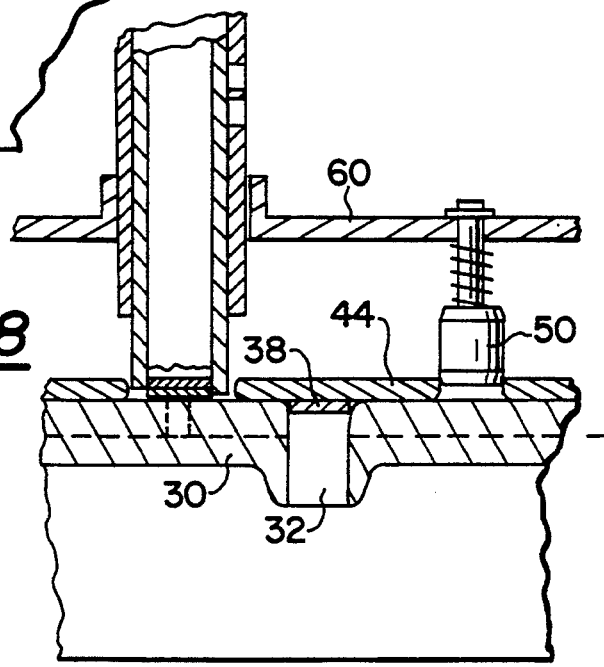
FIG. 8 is a view similar to FIG. 7, with the mechanism in an intermediate, transporting position.

Starting from the stationary or rest position as shown in FIGS. 4 and 7, plunger 14 is depressed downwardly, by applying force to end cap 16. Downwards movement of the plunger causes corresponding downwards movement of actuating pins 26 with consequential rotation of sleeve 24 as the pins slide in the first inclined portions 28a of slots 28. This causes corresponding rotation of transport plate 30 in an anticlockwise direction as seen in FIG. 3, with the remaining components remaining stationary. This movement causes plate 30 and discs 38 carried thereby to rotate relative to the remaining components, with the effect that the discs are rotationally moved from being below the cartridge in a direction towards the associated tamping pins 50 as shown in FIG. 8. The discs 22 are retained in position in plate 30 between rims 34 and faces 42, with the discs being positively located by these components. Retaining plate 44 on top of the transport plate 30 acts to prevent movement of the discs relative to the transport plate on movement. During such movement, the discs sit in the top of the associated dispensing port 32, which is dimensioned to have a diameter slightly less than that of the discs.

Figure 9:
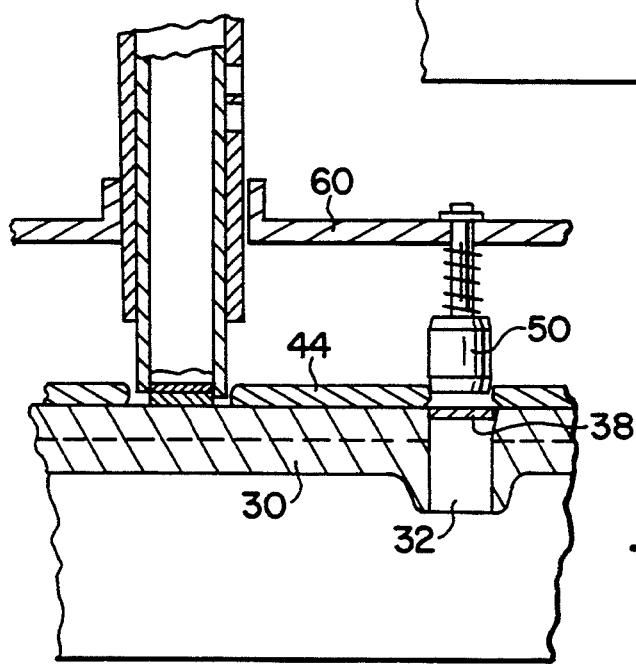
FIG. 9 is a view similar to FIG. 7, with the mechanism in an intermediate position corresponding to that shown in FIG. 5.

Transport plate 30 rotates on depression of plunger 14 until the components reach the position shown in FIGS. 5 and 9, in which the discs and dispensing ports 32 are aligned with the associated tamping pins 50.

The initial part of this rotary movement involves the highest load, so the first portion 28a of each slot is gently sloping to give a good mechanical advantage. The intermediate portion 28b of each slot is more steeply sloping as in this part of the movement there is no need for such a high mechanical advantage.

As shown in FIG. 5, in this intermediate position, the actuating pins 26 now engage flange portion 60 of dispensing plate 52, and further downwards movement of the plunger causes downwards movement of the dispensing plate, pushing the tamping pins 50 through the dispensing ports 32 to expel the discs. No rotary motion takes place in this part of the dispensing action as the slot portions 28c are vertical.

Figure 10:
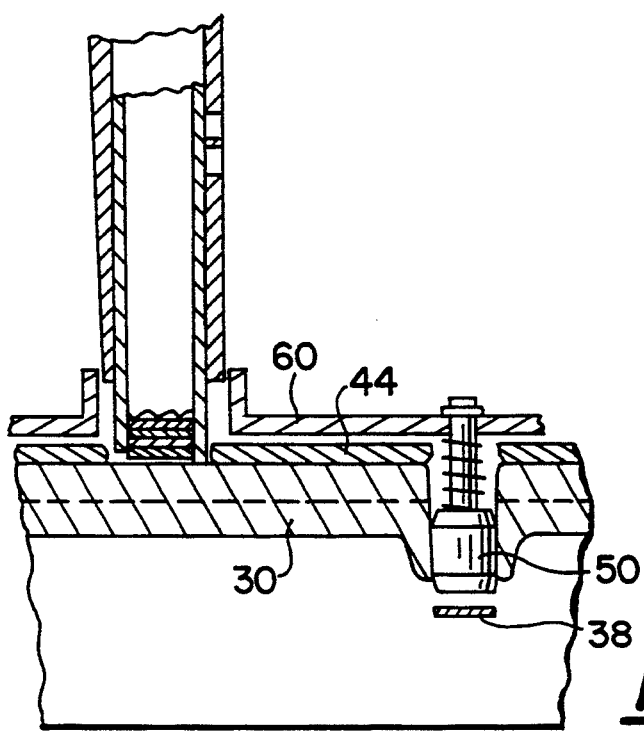
FIG. 10 is a view similar to FIG. 7, with the mechanism in the end or dispensing position.

In the end or dispensing position shown in FIG. 6 and 10, the dispensing plate 52 engages retaining plate 44 and further downwards movement is not possible. In this position, the tamping pins 50 project slightly from the dispensing ports and act to tamp the discs 22 firmly onto the surface of the gel 95 in the petri dish 94.

Before dispensing, the height of the dispenser is adjusted by use of base 12, as described above, to be suited to the thicknesses of the particular gel.

The spring mounting of the tamping pins 50 mean that the device can accommodate some degree of irregularity in the gel thickness.

On release of downwards force from the plunger 14, the return springs 62 and 81 act to return the components to the start position as shown in FIG. 4. The device is then ready for reuse to dispense the next discs from the cartridges.

When a cartridge is empty, the plunger therein protrudes slightly therefrom and engages in the transport plate 30 preventing rotation thereof thus effectively locking the dispenser and preventing use.

If a respective cartridge is not located in each receptacle, the dispenser will nevertheless still function, but in practice the dispenser would always be used with a cartridge in each receptacle.

The dispenser can be stored in the casing supplied when not required for use. If discs are located in the dispenser, the arrangement can be satisfactorily stored under low temperature conditions, for example in a fridge, to retain the active reagents on the discs in suitable condition for use at a later stage.

The case includes a large flat top onto which information concerning the contents can be readily marked.

The dispenser has been found to function well in tests. The dispenser is robust and reliable and little or no problems have arisen due to the mechanism jamming, unlike certain prior art dispensers.

I claim:

1. A dispenser for dispensing flat objects from a stack of similar objects housed in a cartridge, comprising: a body portion; a plurality of receptacles within the body portion, each receptacle being adapted to receive a respective object-containing cartridge; a plurality of dispensing ports, one associated with each receptacle; a plurality of tamping pins, one associated with each dispensing port, for tamping an object through the associated dispensing port; transport means arranged for rotary motion to transport an object from each cartridge in a receptacle to a dispensing position in alignment with the associated tamping pin and dispensing port; retaining means fixed with respect to the receptacles, for retaining the objects in position during transport from a cartridge to the associated dispensing position and a plunger actuator mechanism including a plunger for causing rotary motion of the transport means and tamping motion of the tamping pins on plunging movement of the plunger.

2. A dispenser according to claim 1, wherein the transport means comprises a transport plate arranged for rotary motion, the dispensing ports being carried by the transport plate.

3. A dispenser according to claim 1 or 2, wherein the retaining means comprise a retaining plate, located adjacent the transport means, to contact the adjacent faces of the objects during transport.

4. A dispenser according to claim 3, wherein the retaining plate is in the form of a disc with a first series of apertures through which ends of the cartridges pass and a second series of apertures, interposed between the first series, through which the tamping pins pass.

5. A dispenser according to claim 1, wherein the plunger actuator mechanism comprises a rotary actuating tube fixed with respect to the transport means and including one or more cam slots for receiving a respective actuating pin fixed with respect to a plunger.

6. A dispenser according to claim 5, wherein the or each slot is shaped such that downwards movement of plunger relative to the actuating tube causes initial rotary motion of the actuating tube and hence of the attached transport means, for moving objects to the dispensing position, and subsequent downwards movement of the plunger causes vertical movement of the or each pin, with the pins engaging a dispensing plate and causing downwards dispensing movement of the tamping pins, for causing dispensing of the objects.

7. A dispenser according to claim 6, wherein the or each slot includes three sections: a first slightly inclined portion; a second more inclined portion; and a third vertical portion.

8. A dispenser according to claim 7, further comprising a removable base (12), for height adjustment purposes.

9. A dispenser according to claim 8, wherein the base has a stepped upper face adapted to be engaged by ribs in the body portion such that relative rotation of the body and base results in adjustment in the height of the base above a surface.

10. A dispenser according to claim 9, adapted for use in dispensing sensivity or susceptibility test discs from cylindrical cartridges.

11. A dispenser according to claim 1, wherein the tamping pins are moved by the action of a dispensing plate, being biased to a non-dispensing position by spring means acting between the dispensing plate and the retaining means, both the dispensing plate and the retaining means being rotationally stationary during operation of the dispenser.

* * * * *